United States Patent
Maunz et al.

(10) Patent No.: US 12,300,384 B2
(45) Date of Patent: May 13, 2025

(54) METHODS AND SYSTEMS FOR THERAPEUTIC RESPONSE PREDICTION

(71) Applicant: HOFFMANN-LA ROCHE INC., Little Falls, NJ (US)

(72) Inventors: Andreas Maunz, Basel (CH); Ian Lloyd Jones, Basel (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 605 days.

(21) Appl. No.: 17/502,911

(22) Filed: Oct. 15, 2021

(65) Prior Publication Data

US 2022/0122733 A1 Apr. 21, 2022

Related U.S. Application Data

(60) Provisional application No. 63/092,427, filed on Oct. 15, 2020.

(51) Int. Cl.
| | |
|---|---|
| *G06K 9/00* | (2022.01) |
| *G06F 18/214* | (2023.01) |
| *G06T 7/00* | (2017.01) |
| *G16H 10/20* | (2018.01) |
| *G16H 50/20* | (2018.01) |

(52) U.S. Cl.
CPC ........... *G16H 50/20* (2018.01); *G06F 18/214* (2023.01); *G06T 7/0016* (2013.01); *G16H 10/20* (2018.01); *G06T 2207/30041* (2013.01)

(58) Field of Classification Search
CPC ........ G16H 50/20; G16H 10/20; G16H 70/40; G16H 20/10; G16H 50/70; G06N 20/00; G06N 3/02; G06V 2201/03; G06V 10/82; G06V 10/40; G06T 7/0012; G06T 2207/30041; G06T 7/0016; A61B 5/7264; A61B 3/102; G06F 18/214
See application file for complete search history.

(56) References Cited

U.S. PATENT DOCUMENTS

| | | | |
|---|---|---|---|
| 10,722,180 B2 * | 7/2020 | Zhang | G06N 3/045 |
| 2021/0244272 A1 * | 8/2021 | Lim | G16H 30/20 |
| 2022/0230300 A1 * | 7/2022 | Kawczynski | G06T 7/0004 |
| 2023/0025980 A1 * | 1/2023 | Kawczynski | G06T 7/187 |

FOREIGN PATENT DOCUMENTS

| | | | | |
|---|---|---|---|---|
| WO | WO-2021220138 A1 * | 11/2021 | | A61B 3/0025 |

* cited by examiner

*Primary Examiner* — Gregory A Morse
*Assistant Examiner* — Kevin M Coomber
(74) *Attorney, Agent, or Firm* — HAYNES AND BOONE, LLP

(57) ABSTRACT

Embodiments described herein provide methods and systems for predicting a subject response to a therapeutic. The methods and systems generally operate by using a machine learning (ML) component trained using time-series responses and image features to generate time-series responses of a subject to a therapeutic that has been administered to the subject.

20 Claims, 15 Drawing Sheets

```
┌──────────────────────────────────────────────────┐
│  Receive image feature data from at least one    │
│  time point associated with an administration    │
│  of a therapeutic to at least one test subject   │
└──────────────────────────────────────────────────┘
                         │
                         ▼
┌──────────────────────────────────────────────────┐
│ Generate a plurality of predicted time-series    │
│ responses of the at least one test subject to    │
│ the administered therapeutic using a machine     │
│ learning (ML) component                          │
└──────────────────────────────────────────────────┘
```

210 — Receive image feature data from at least one time point associated with an administration of a therapeutic to at least one test subject 220 — Generate a plurality of predicted time-series responses of the at least one test subject to the administered therapeutic using a machine learning (ML) component

# METHODS AND SYSTEMS FOR THERAPEUTIC RESPONSE PREDICTION

CROSS-REFERENCE

The present application claims priority to U.S. Provisional Patent Application No. 63/092,427, filed on Oct. 15, 2020, entitled "METHODS AND SYSTEMS FOR THERAPEUTIC RESPONSE PREDICTION," which application is herein incorporated by reference in its entirety for all purposes.

TECHNICAL FIELD

The present disclosure relates generally to methods and systems for predicting a response to a therapeutic.

INTRODUCTION

There is a need for pharmaceuticals, biologics, drugs, or other therapeutics that target populations who do not respond positively to existing treatments. In clinical trials for such therapeutics, the composition of patients involved in the trial is crucial. For instance, it makes little sense to include patients who respond well to an existing treatment. Rather, the trial composition should emphasize patients who do not respond well to existing treatments. If a particular patient's response to existing treatments can be predicted, a person conducting a clinical trial may be able to better choose whether to include that patient in the clinical trial. In addition, a healthcare practitioner may better select treatment and treatment frequency for the patient, if a patient response to treatment may be predicted.

Furthermore, a particular patient may respond well to a particular therapeutic, a particular dosage of a therapeutic, and/or a particular frequency of administration of a therapeutic. The same patient may not respond well to a different therapeutic, dosage, and/or frequency of administration. If a particular patient's response to a therapeutic, dosage, and/or frequency of administration can be predicted, a healthcare professional may be able to better choose which course of treatment to pursue for the patient. As such, there is a need for methods and systems for predicting a response to a therapeutic.

Figure 1A:
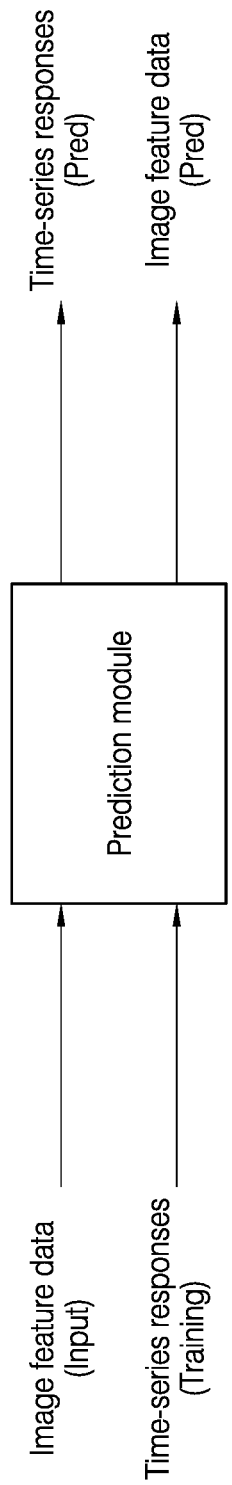
FIG. 1A is a simplified diagram of a process flow for predicting a subject response to a therapeutic, in accordance with various embodiments.

In various embodiments, not all of the depicted components in each figure may be required, and various embodiments may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

This specification describes exemplary methods and systems for predicting a subject response to a therapeutic. Current response prediction models may include pharmacokinetic/pharmacodynamic models or computational models that do not have intrinsic time parameters. For such models to make predictions, training for the models may entail using data that is collected over time, or data with embedded time parameters. Such data may not be available. Alternately, such data may be difficult to obtain, especially prior to conducting a clinical trial. Accordingly, a desire exists for a response prediction model that may account for temporal relationships.

The methods and systems may operate by using a machine learning (ML) component trained using time-series responses to therapeutics and time-series image features to generate predictions of time-series responses of a subject to a therapeutic that has been administered to the subject. Time series responses may include any clinical measurements, including situations in which there is no change in a measurement (e.g., BCVA), over a period of time. In particular, the present embodiments may entail using a recurrent neural network to generate the predictions of responses of a subject according to a time series. The present recurrent neural networks may intrinsically contain a time-dependent serial component such that connections are made from input patient training data, along a temporal sequence. The recurrent neural networks may permit predictions and learnings of dynamic responses and behavior, along a temporal scale or parameter. Accordingly, the present recurrent neural networks may receive subject-related data at a single time point or at multiple time points and then generate predictions of time-series responses of the subject to a therapeutic. The intrinsic serial component of the recurrent neural network may provide enhanced predictive capabilities.

The methods and systems may have particular utility in the development of therapeutics for treating ophthalmic disorders, though the disclosure herein is not limited to such applications. For instance, many patients may respond well to the drug ranibizumab for treating of macular degeneration (MD). Patients may have BCVA scores that indicate an improvement in visual acuity after treatment—e.g., improved BCVA scores over time. However, a subset of patients may not respond well to ranibizumab. For example, patients may have BCVA scores that indicate a lack of improvement in visual acuity after treatment—e.g., unchanged BCVA scores or lower BCVA scores over time. For such patients, there is a need for new MD treatments. However, this subset of patients may be a minority of all patients. Thus, if a clinical trial cohort is representative of the general population, the response of this subset may be drowned out by the response of the majority of patients who respond well to ranibizumab. A properly selected cohort would mainly include the subset of patients who do not respond well to ranibizumab. The systems and methods described herein can be used to predict a subject's response to ranibizumab. If the subject is predicted to respond well to ranibizumab, the subject can be excluded from the clinical trial. If, on the other hand, the subject is predicted to not respond well to ranibizumab, the subject can be included in the clinical trial. Moreover, the methods and systems may have particular utility in predicting a subject's response to a particular therapeutic for treating an ophthalmic disorder, dosage of the therapeutic, and/or frequency of administration of the therapeutic. This individualized response prediction may aid healthcare professionals in selecting treatment and treatment frequency for a given patient, and facilitate clinical study design.

FIG. 1A is a simplified exemplary diagram of a process flow for predicting a subject response to a therapeutic. According to various embodiments, one or more processors receive image feature data from at least one time point associated with an administration of the therapeutic to at least one test subject. The one or more processors may generate a plurality of predicted time-series responses of the at least one subject to the administered therapeutic using a ML component. The ML component may be trained using a training data set comprising a plurality of time-series responses or other clinical measurements and corresponding image features of at least one training subject after an administration of the therapeutic.

In various embodiments, the ML component comprises a neural network (NN). The NN may comprise a recurrent NN (RNN). The training data set may further comprise at least one age of the at least one training subject. The plurality of time-series responses of the at least one training subject may comprise a plurality of best corrected visual acuity (BCVA) scores. The plurality of time-series responses of the at least one test subject may comprise a plurality of BCVA scores.

In various embodiments, the image features or the image feature data comprises at least one parameter obtained from at least one optical coherence tomography (OCT) image. The at least one OCT image may comprise at least one spectral domain-OCT (SD-OCT) image. The parameter may comprise an intraretinal fluid (IRF) value, a subretinal fluid (SRF) value, a subretinal hyperreflective material (SHRM) value, or a pigment epithelial detachment (PED) value.

In various embodiments, the image features or the image feature data comprises at least one parameter obtained from at least on medical imaging image. The at least one medical imaging image may comprise a magnetic resonance imaging (MRI) image, a computed tomography (CT) image, an ultrasound image, or a positron emission tomography (PET) image.

In various embodiments, the therapeutic comprises administration of a drug. The drug may correspond to an ophthalmic disorder. The drug may comprise ranibizumab. The ophthalmic disorder may comprise a macular degeneration (MD) disorder. The MD disorder may comprise an age-related MD disorder. The age-related MD disorder may comprise a subfoveal neovascular age-related MD (nAMD) disorder.

In various embodiments, the one or more processors receive a training data set comprising a plurality of time-series responses and corresponding image features from at least one training subject after an administration of a therapeutic and train the ML component using the training data set. In various embodiments, each corresponding image feature is associated with a time-series response of the plurality of time-series responses.

Figure 1B:
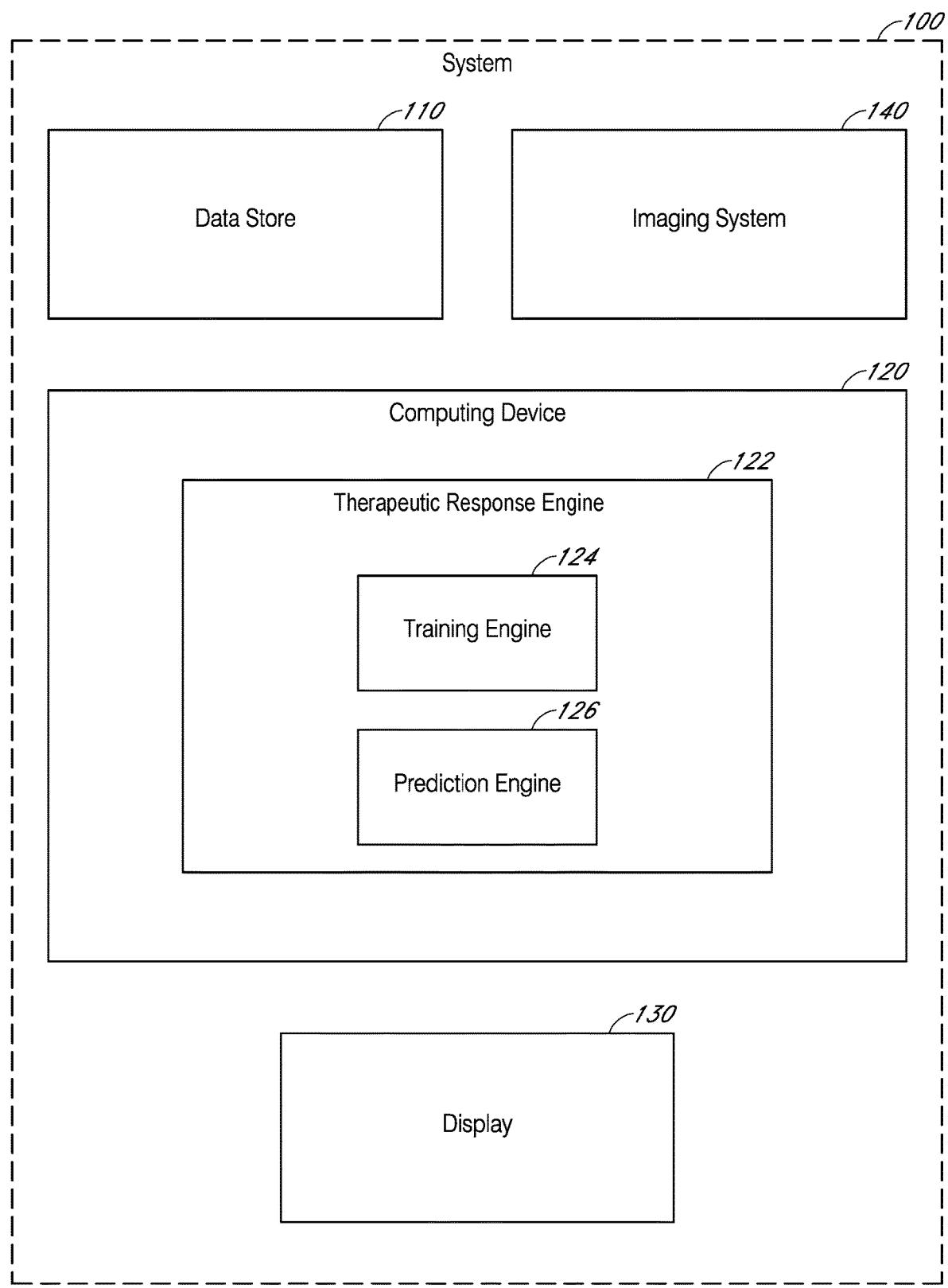
FIG. 1B is a schematic diagram of a system for predicting a subject response to a therapeutic, in accordance with various embodiments.

FIG. 1B is a schematic diagram of a system 100 for predicting a subject response to a therapeutic, in accordance with various embodiments. System 100 can include a data store 110, a computing device 120, and a display 130. System 100 can also include an imaging system 140. However, system 100 need not include the imaging system 140.

Data store 110 can be communicatively connected to the computing device 120. In various embodiments, the computing device 120 can be communicatively connected to the data store 110 via a network connection that can be either a "hardwired" physical network connection (e.g., Internet, LAN, WAN, VPN, etc.) or a wireless network connection (e.g., Wi-Fi, WLAN, etc.). In various embodiments, the computing device 120 can be a workstation, mainframe computer, distributed computing node (part of a "cloud computing" or distributed networking system), personal computer, mobile device, etc. The data store 110 can be configured to receive image feature data. For instance, the data store can be configured to receive image feature data from the imaging system 140.

Computing device 120 can further include a therapeutic response engine 122, a prediction training engine 124, and a prediction engine 126. The therapeutic response engine 122 can comprise the prediction training engine 124 and the prediction engine 126. The prediction training engine 124 can be configured to train an ML model using a training dataset comprising a plurality of time-series responses and corresponding image features of at least one training subject after an administration of a therapeutic. For instance, each time-series response may be associated with at least one image feature representing or reflecting the at least one training subject's state, after the therapeutic was administered to the patient. The ML model may comprise an ML component described herein with respect to FIG. 1A, an ML model described herein respect to method 200 of FIG. 2, an RNN described herein with respect to FIG. 3, or any other ML process described herein. The prediction training engine 124 can be trained as described herein with respect to FIG. 4 or using any other training process described herein. The prediction engine 126 can be configured to receive the ML model from the training engine and to generate a plurality of predicted time-series responses of the at least one test subject to the administered therapeutic using the ML model. For instance, the prediction engine can be configured to generate the plurality of predicted time-series responses as described herein with respect to FIG. 3.

After the plurality of predicted time-series responses of the at least one test subject to the administered therapeutic has been determined, it can be displayed as a result or summary on the display 130 or on a client terminal that is communicatively connected to the computing device 120. In various embodiments, the display 130 can be a thin client computing device. In various embodiments, the display 130 can be a personal computing device having a web browser (e.g., INTERNET EXPLORER™, FIREFOX™ SAFARI™ etc.) that can be used to control the operation of the therapeutic response engine 122, the prediction training engine 124, and the prediction engine 126.

It should be appreciated that the various engines can be combined or collapsed into a single engine, component, or module, depending on the requirements of the particular application or system architecture. In various embodiments the therapeutic response engine 122, the prediction training engine 124, and the prediction engine 126 can comprise additional engines or components as needed by the particular application or system architecture.

Imaging system 140 can be communicatively connected to the data store 110 by way of a serial bus (if both form an integrated instrument platform) or by way of a network connection (if both are distributed/separate devices). Imaging system 140 can be configured to obtain image feature data from at least one time point associated with an administration of the therapeutic to at least one test subject. The imaging system can comprise an OCT imaging system or an SD-OCT imaging system. The image feature data can comprise at least one OCT image or at least one SD-OCT image. In various embodiments, the image feature data can then be stored in the data store 110 for subsequent processing. In various embodiments, the image feature data can be input into the computing device 120 in real-time. In various embodiments, the image feature data can also be stored in the data store 110 prior to processing. In various embodiments, the image feature data can also be input into the computing device 120 in real-time.

In some embodiments, the imaging system is further configured to at least partially measure the training data set by measuring at least a portion of the plurality of time-series responses of the at least one training subject and the corresponding image features.

Figure 2:
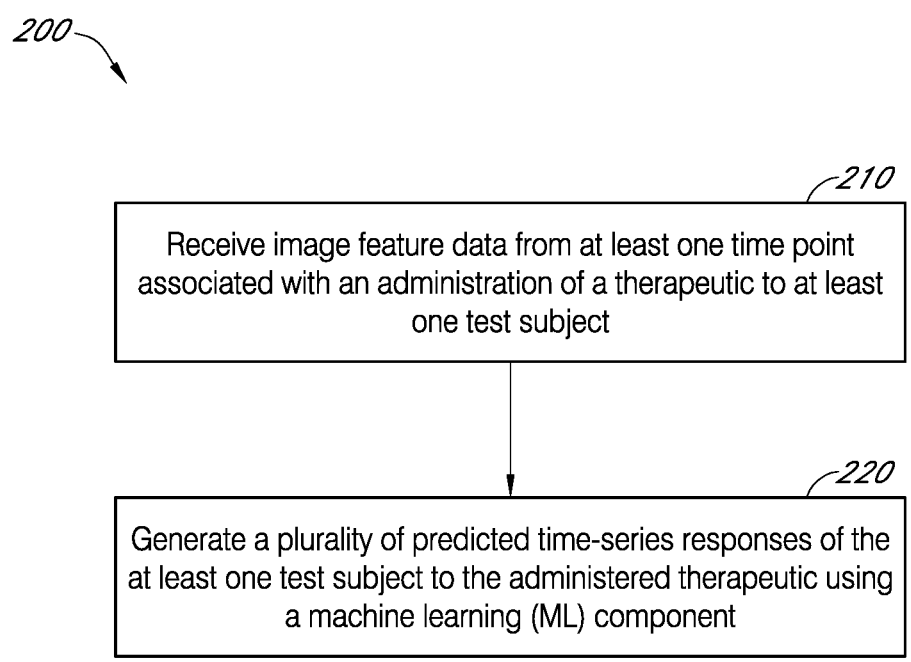
FIG. 2 is a simplified diagram of a method for predicting a subject response to a therapeutic, in accordance with various embodiments.

FIG. 2 is a simplified diagram of a method 200 for predicting a subject response to a therapeutic. In various embodiments, the method 200 comprises a first step 210 of receiving (for instance, by one or more processors) image feature data from at least one time point associated with an administration of a therapeutic to at least one test subject. In some embodiments, the at least one time point comprises at least about 1, 2, 3, 4, 5, 6, 7, 8, 9, 10, or more time points associated with at least about 1, 2, 3, 4, 5, 6, 7, 8, 9, 10, or more administrations of the therapeutic to the at least one test subject. In some embodiments, the at least one time point comprises at most about 10, 9, 8, 7, 6, 5, 4, 3, 2, or 1 time points associated with at most about 10, 9, 8, 7, 6, 5, 4, 3, 2, or 1 administrations of the therapeutic to the at least one test subject. In some embodiments, the at least one time point comprises a number of time points that is within a range defined by any two of the preceding values. For example, in some embodiments, the at least one time point corresponds to 1 or 2 administrations of the therapeutic to a subject at 1 or 2 medical office visits.

In various embodiments, the method 200 comprises a second step 220 of generating (for instance, by the one or more processors) a plurality of predicted time-series responses of the at least one test subject to the administered therapeutic using a ML component. The ML component may be trained using a training data set comprising a plurality of time-series responses or other clinical measurements and corresponding image features of at least one training subject after and administration of the therapeutic. In some embodiments, the plurality of predicted time-series responses comprises at least about 2, 3, 4, 5, 6, 7, 8, 9, 10, 20, 30, 40, 50, 60, 70, 80, 90, 100, or more predicted time-series responses. In some embodiments, the plurality of predicted time-series responses comprises at most about 100, 90, 80, 70, 60, 50, 40, 30, 20, 10, 9, 8, 7, 6, 5, 4, 3, or 2 predicted time series responses. In some embodiments, the plurality of predicted time-series responses comprises a number of time-series responses that is within a range defined by any two of the preceding values. For example, in some embodiments, the plurality of time-series responses comprises daily, weekly, or monthly predicted therapeutic responses for a period of days, weeks, month, or years following the first 1 or 2 office visits.

In some embodiments, the method 200 further comprises generating the training data set by measuring the plurality of time-series responses of the at least one training subject and the corresponding image features. In some embodiments, the training data set is at least partially generated using the imaging system described herein with respect to FIG. 1B.

Figure 3:
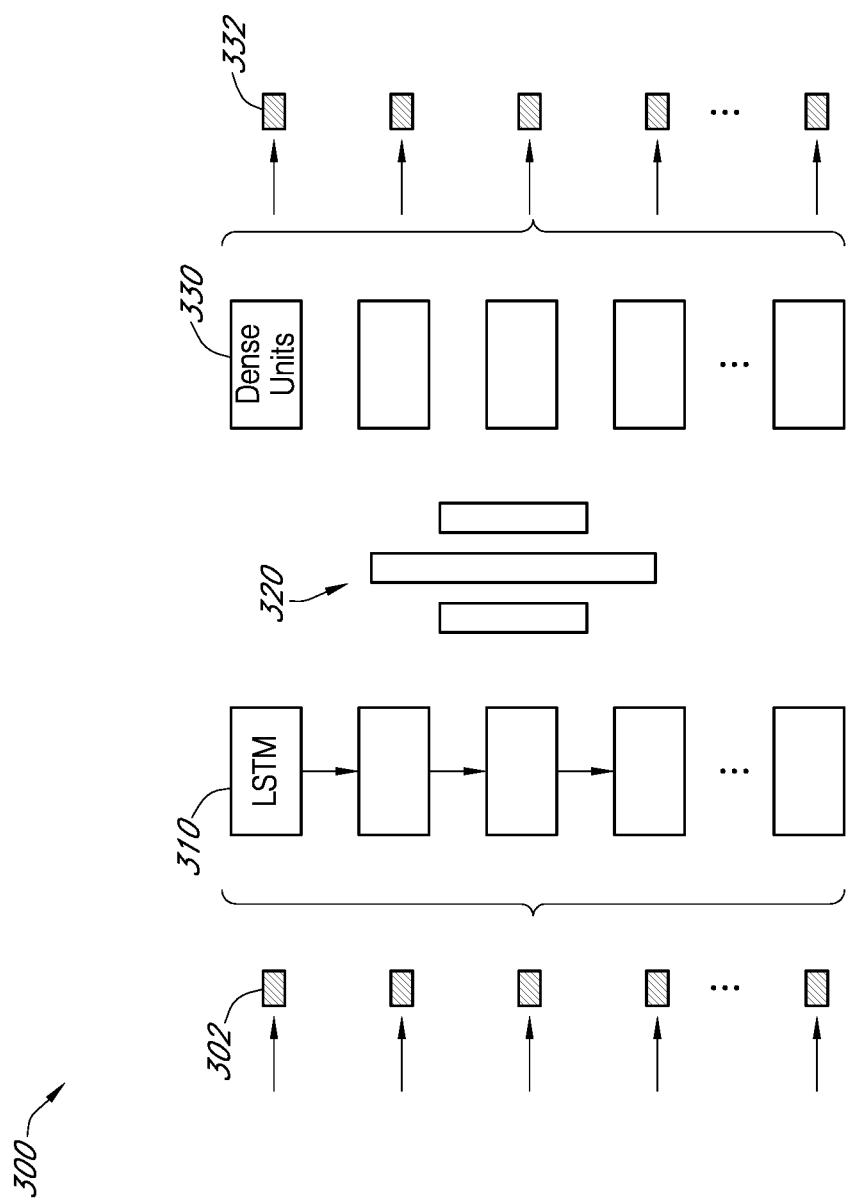
FIG. 3 is a block diagram of a recurrent neural network (RNN) for use with the systems and methods of FIGS. 1A and 2, in accordance with various embodiments.

FIG. 3 is a block diagram of a recurrent neural network (RNN) 300 for use with the systems and methods of FIGS. 1A and 2. As shown in FIG. 3, the RNN 300 can be comprised of an input layer 310, one or more inner layers 320, and an output layer 330.

In various embodiments, the input layer 310 is configured to ingest image feature data 302 (such as any image feature data described herein with respect to FIGS. 1A, 1B, and/or 2) so that the data can be processed by the RNN 310. In various embodiments, the input layer can be configured to ingest additional inputs besides image feature data, such as, but not limited to time-series responses (such as any time-series responses described herein). In various embodiments, the input layer is configured to apply long short-term memory (LSTM) to the image feature data.

In various embodiments, the hidden layers 320 comprise at least about 1, 2, 3, 4, 5, 6, 7, 8, 9, 10, or more layers of nodes. In various embodiments, the hidden layers comprise at most about 10, 9, 8, 7, 6, 5, 4, 3, 2, or 1 layers of nodes. In various embodiments, the hidden layers comprise a number of layers of nodes that is within a range defined by any two of the preceding values. In various embodiments, the number of hidden layers and/or the number of nodes in the hidden layers is preset prior to training. In various embodiments, the number of hidden layers and/or the number of nodes in the hidden layers is automatically set by the RNN 300 during.

In various embodiments, the output layer 330 can be configured to output output values 332. The output values may comprise any predicted time-series responses and/or corresponding image features described herein with respect to FIGS. 1A, 1B, and/or 2. Output values 332 may include predicted BCVA values over time after a baseline time point at which the therapeutic is administered (e.g., a dose of the therapeutic is administered). Predicted BCVA values that increase over time after the baseline time point can indicate an improvement in visual acuity, which may, in turn, indicate that the subject is responding well to treatment. Predicted BCVA values that do not generally change or that decrease over time can indicate a lack of improvement in visual acuity, which may, in turn, indicate that the subject is not responding well to treatment.

At a high level, the RNN 300 operates by finding the correct mathematical manipulation (through "learning" using any training data described herein) to turn the input of a preceding layer (i.e., either the input layer or any inner layer) into the output of a subsequent layer (i.e., either the output layer or any inner layer). This occurs regardless of whether the mathematical manipulation is a linear relationship or a non-linear relationship. The RNN "learns" by adjusting the weights (and optional thresholds) of the nodes in the various layers of the RNN to improve the accuracy of the result. Learning is complete when examining additional observations (of training data) does not usefully reduce the error rate or reduces the error rate to some pre-defined value. Complex RNNs may have many layers, and thus may be referred to as "deep" RNNs.

After learning (training) and during model use (prediction), the RNN serves to relate an input set of data (such as the image feature data and/or time-series responses of at least one training subject described herein with respect to FIGS. 1A, 1B, and/or 2) to an output set of data (such as the predicted time-series responses and/or corresponding image features described herein with respect to FIGS. 1A, 1B, and/or 2) via a mathematical function and the previously trained weights. During prediction, the weights are fixed and the input data and numerical values of the weights together with the architecture of the layers of the RNN represent the mathematical function relating how the input data and weights are computed together to calculate the outputs of the RNN.

Figure 4:
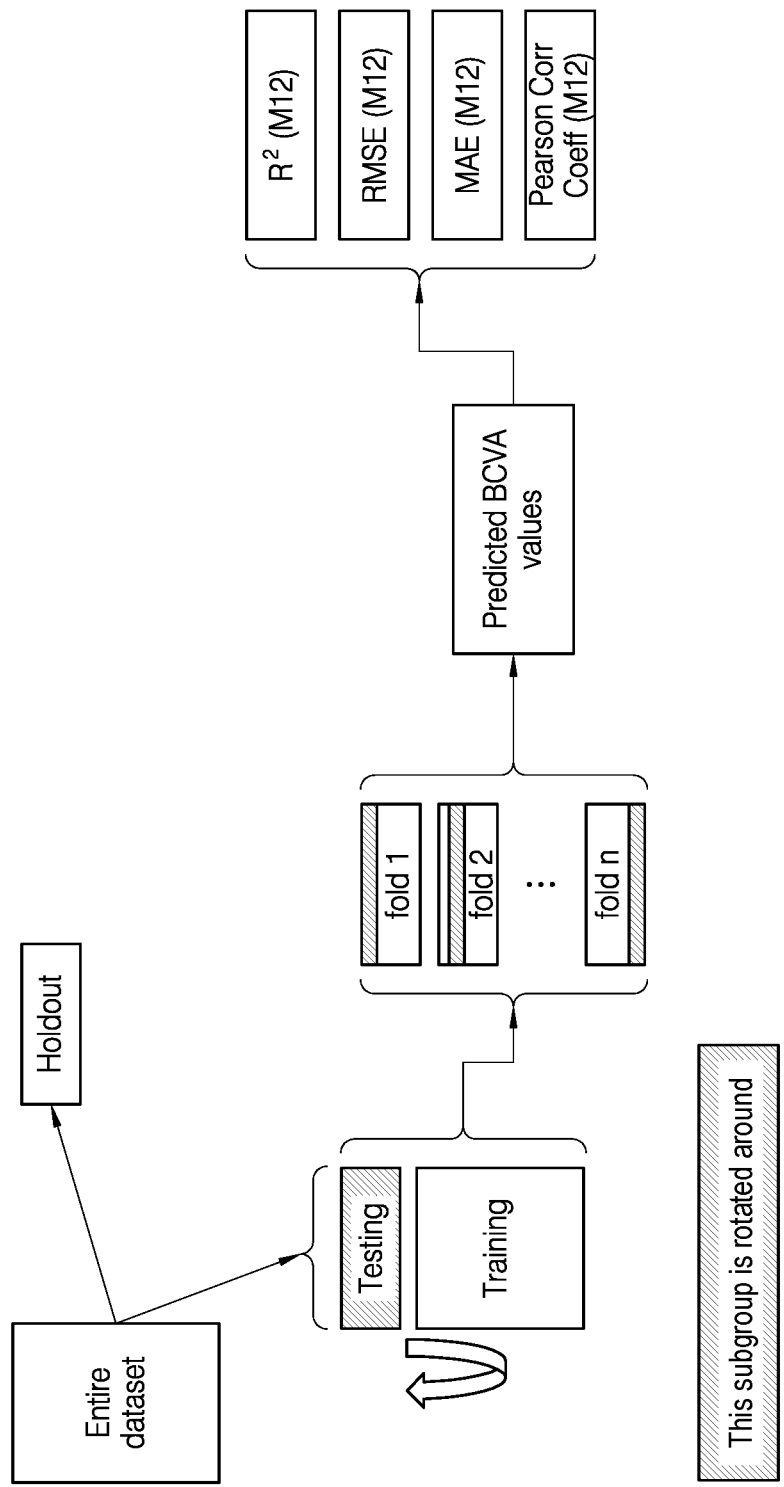
FIG. 4 is a block diagram of an RNN training procedure associated with the RNN of FIG. 3, in accordance with various embodiments.

FIG. 4 is a block diagram of an RNN training procedure associated with the RNN of FIG. 3. During a learning phase, the RNN can be trained to predict the predicted time-series responses and/or corresponding image feature data described herein with respect to FIGS. 1A, 1B, and/or 2. During the training phase, a dataset (such as the image feature data and/or time-series responses of at least one training subject described herein with respect to FIGS. 1A, 1B, and/or 2) used to train the RNN (referred to as an "entire dataset" in FIG. 4) may be divided into a first portion used for testing and training and a second portion that is held out (referred to as a "holdout" set) for later assessment of the trained RNN. The first portion may comprise at least about 5%, 10%, 15%, 20%, or more of the entire dataset. The first portion may comprise at most about 20%, 15%, 10%, 5%, or less of the entire dataset. The first portion may comprise a percentage of the entire dataset that is within a range defined by any two of the preceding values. The second portion may comprise at least about 80%, 85%, 90%, 95%, or more of the entire dataset. The second portion may comprise at most about 95%, 90%, 85%, 80%, or less of the entire dataset. The second portion may comprise a percentage of the entire dataset that is within a range defined by any two of the preceding values.

The first portion may be further divided into a training dataset and a testing dataset. The training dataset may be used to train the RNN. The testing dataset may be used to test the performance of the RNN following training with the dataset. The training dataset may comprise at least about 70%, 75%, 80%, 85%, 90%, 95%, or more of the second portion. The training dataset may comprise at most about 95%, 90%, 85%, 80%, 75%, 70%, or less of the second portion. The training dataset may comprise a percentage of the second portion that is within a range defined by any two of the preceding values. The testing dataset may comprise at least about 5%, 10%, 15%, 20%, 25%, 30%, or more of the second portion. The testing dataset may comprise at most about 30%, 25%, 20%, 15%, 10%, 5%, or less of the second portion. The testing dataset may comprise a percentage of the second portion that is within a range defined by any two of the preceding values. The training and testing datasets may be "rotated around," so that different subsets of the second portion are successively used for training and testing. For instance, if the testing set comprises 20% of the second portion, the second portion may be broken into five equal sets of 20% of the second portion. For each of these five equal sets, the RNN may be trained using the remaining 80% of the second portion. This procedure may result in five different RNNs trained on five slightly different trainings sets. Each of the five different RNNs may be tested using the associated subset and assessed on a variety of error metrics. The best-performing RNN of the five may then be adopted and implemented as described in FIG. 3.

The best-performing RNN may be subjected to n-fold validation, where n is any integer. For instance, the best-performing RNN may be subjected to 1-, 2-, 3-, 4-, 5-, 6-, 7-, 8-, 9-, 10-, or higher-fold validation. The best-performing RNN may be subjected to 10-, 9-, 8-, 7-, 6-, 5-, 4-, 3-, 2-, or 1-fold validation.

Finally, the best-performing RNN may be applied to the holdout dataset to predict the output data (such as the predicted time-series responses and/or corresponding image features described herein with respect to FIGS. 1A, 1B, and/or 2) associated with the holdout dataset. The predicted output data may be compared with "ground truths" (such as the actual time-series responses and/or corresponding image features) associated with the holdout dataset using a variety of statistical metrics. For instance, the metrics may comprise any one or more of an $R^2$ value, a root-mean squared error (RMSE), a mean absolute error (MAE), and a Pearson correlation coefficient.

In describing the various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments. Similarly, any of the various system embodiments may have been presented as a group of particular components. However, these systems should not be limited to the particular set of components, now their specific configuration, communication and physical orientation with respect to each other. One skilled in the art should readily appreciate that these components can have various configurations and physical orientations (e.g., wholly separate components, units and subunits of groups of components, different communication regimes between components).

Although specific embodiments and applications of the disclosure have been described in this specification, these embodiments and applications are exemplary only, and many variations are possible.

EXAMPLES

Example 1. Application of Recurrent Neural Networks in Ophthalmic Image Analysis for Longitudinal Clinical Studies A recurrent neural network (RNN) was trained on the HARBOR clinical dataset. This publicly available dataset represented a phase III, double-masked, multi-center, randomized clinical trial. The clinical trial functioned as an active treatment-controlled study of the efficacy and safety of ranibizumab. Ranibizumab was administered monthly or on an as-needed basis at doses of 0.5 milligrams (mg) or 2 mg. The dataset encompassed a cohort of 1,097 patients with subfoveal neovascular age-related macular degeneration (nAMD).

Figure 5:
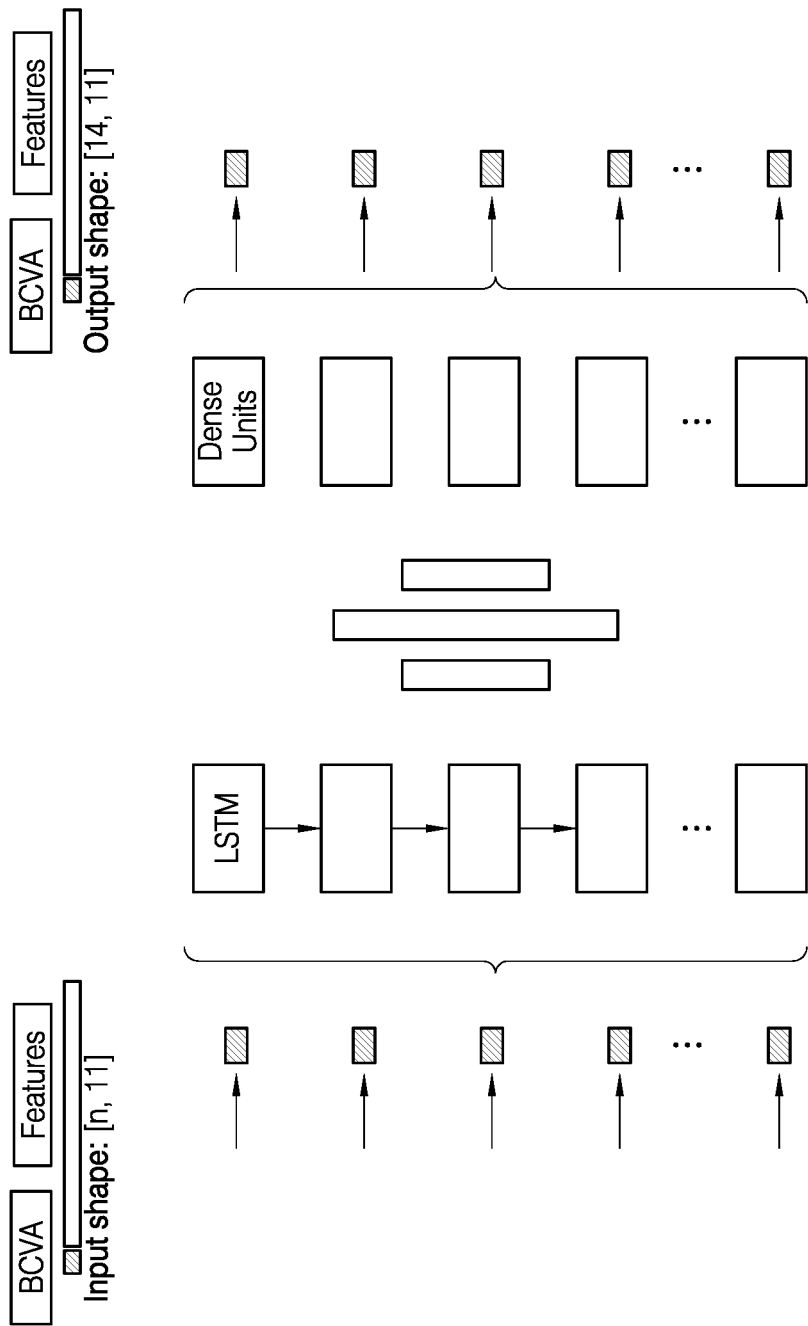
FIG. 5 is a block diagram of an RNN trained on the HARBOR clinical dataset, in accordance with various embodiments.

The block diagram of FIG. 5 is an exemplary diagram of the RNN trained on the HARBOR clinical dataset. The RNN consisted of a 5-layer network with a 14 dense unit input layer, inner layers of 128 dense units (employing long short-term memory, LSTM), 256 dense units, and 128 dense units, and a 14 dense unit output layer. The input training data was a 14×11 vector corresponding to best corrected visual acuity (BCVA) and 10 other visual features acquired at a single office visit. The output data was a 14×11 vector corresponding to 13 predicted BCVA values acquired over a number of office visits. The RNN consisted of a total of 69,887 trainable parameters.

Figure 6:
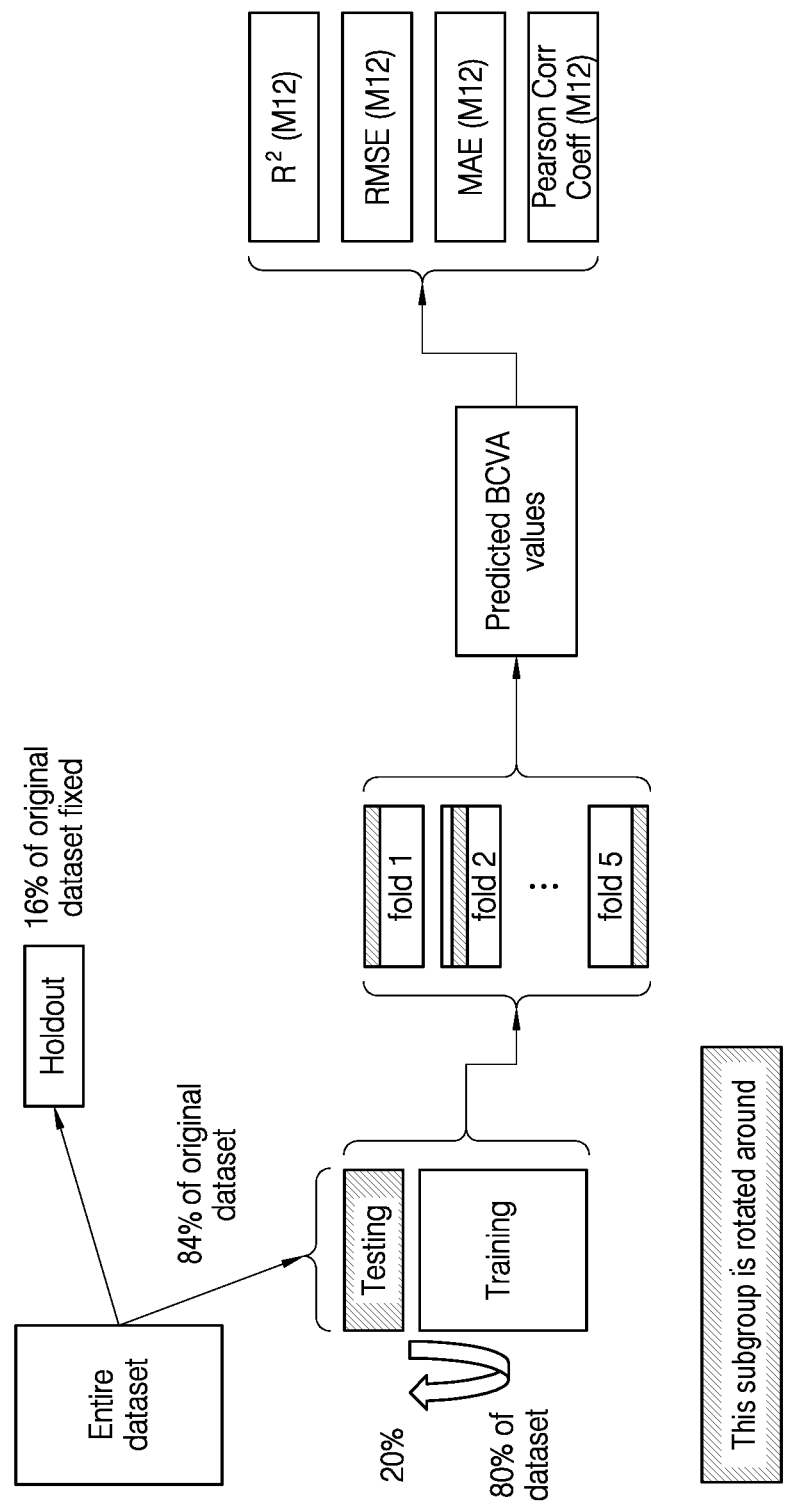
FIG. 6 is a block diagram of an RNN training procedure associated with the RNN of FIG. 5, in accordance with various embodiments.

The block diagram of FIG. 6 is an exemplary diagram of the RNN training procedure of the present application. During training, 16% of the HARBOR dataset was kept as a holdout set and 84% of the HARBOR dataset was kept as a non-holdout set for training and testing. 80% of the non-holdout set was used for training and 20% of the non-holdout set was used for testing. During training, the RNN was subjected to five-fold validation. The training procedure resulted in five different models, from which the best model was selected. The best model was then used to predict BCVA values from the holdout set. The model accuracy was assessed on a variety of metrics, including $R^2$, root mean square error (RMSE), mean absolute error (MAE), and Pearson correlation coefficient.

Figure 7:
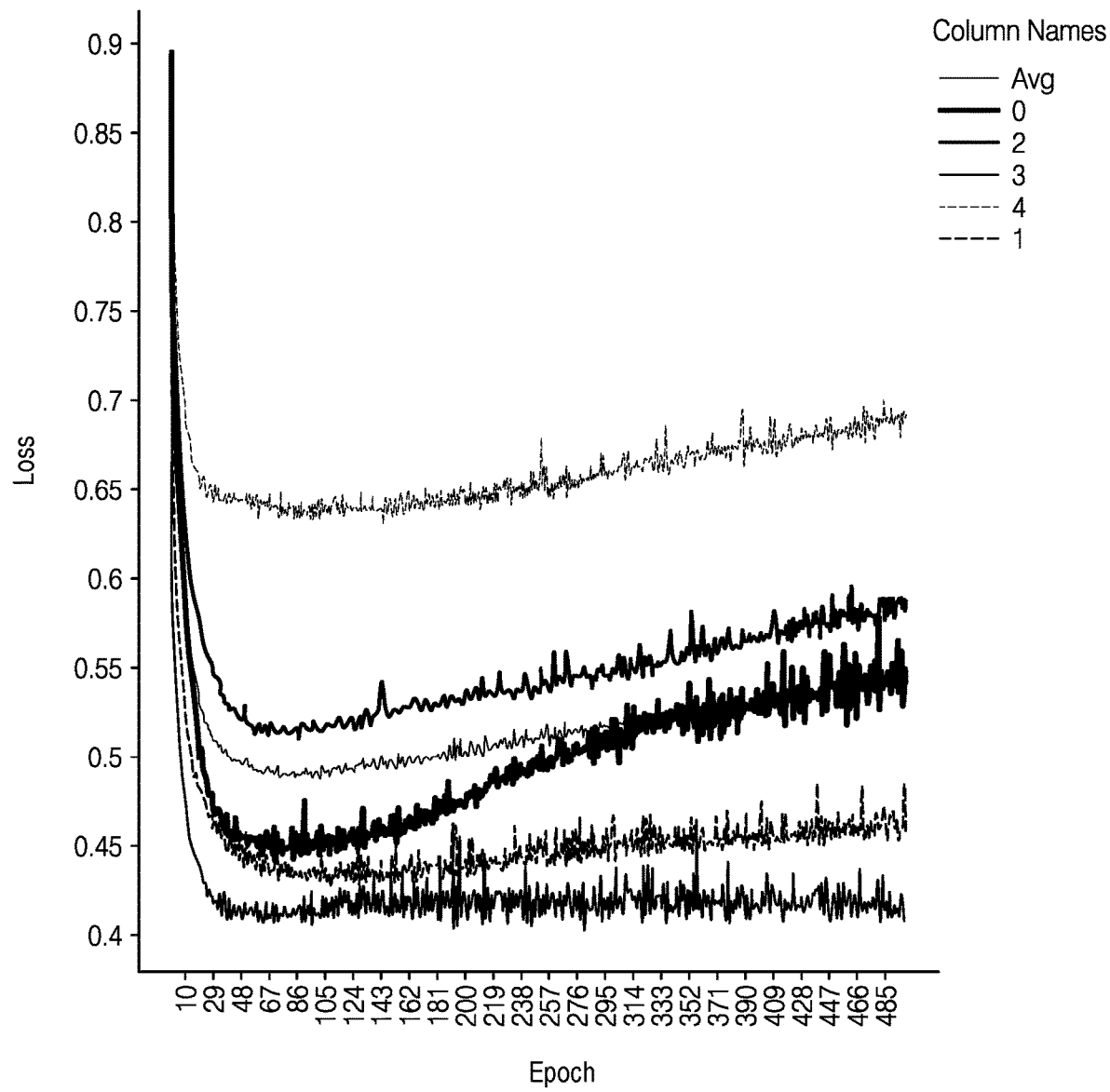
FIG. 7 shows loss curves for 5-fold validation of the RNN, in accordance with various embodiments.

FIG. 7 shows loss curves for 5-fold validation of the RNN. As shown in FIG. 6, after 101 epochs, the best model achieved a loss of approximately 0.4. On average, the five models achieved a loss of approximately 0.49.

Figure 8:
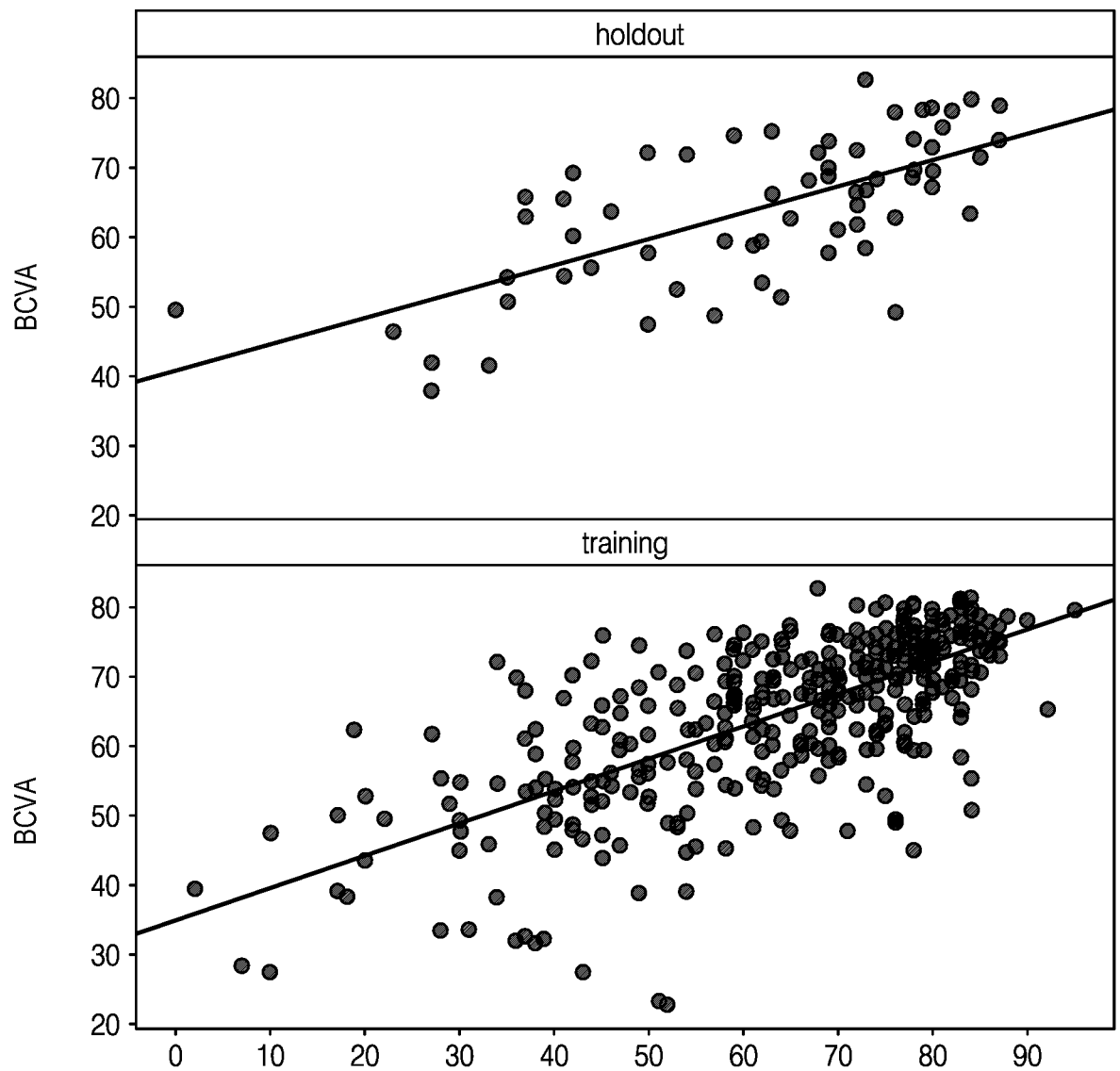
FIG. 8 shows best corrected visual activity (BCVA) values predicted by the RNN versus observed BCVA values for a holdout dataset and a training dataset, in accordance with various embodiments.
Figure 9A:
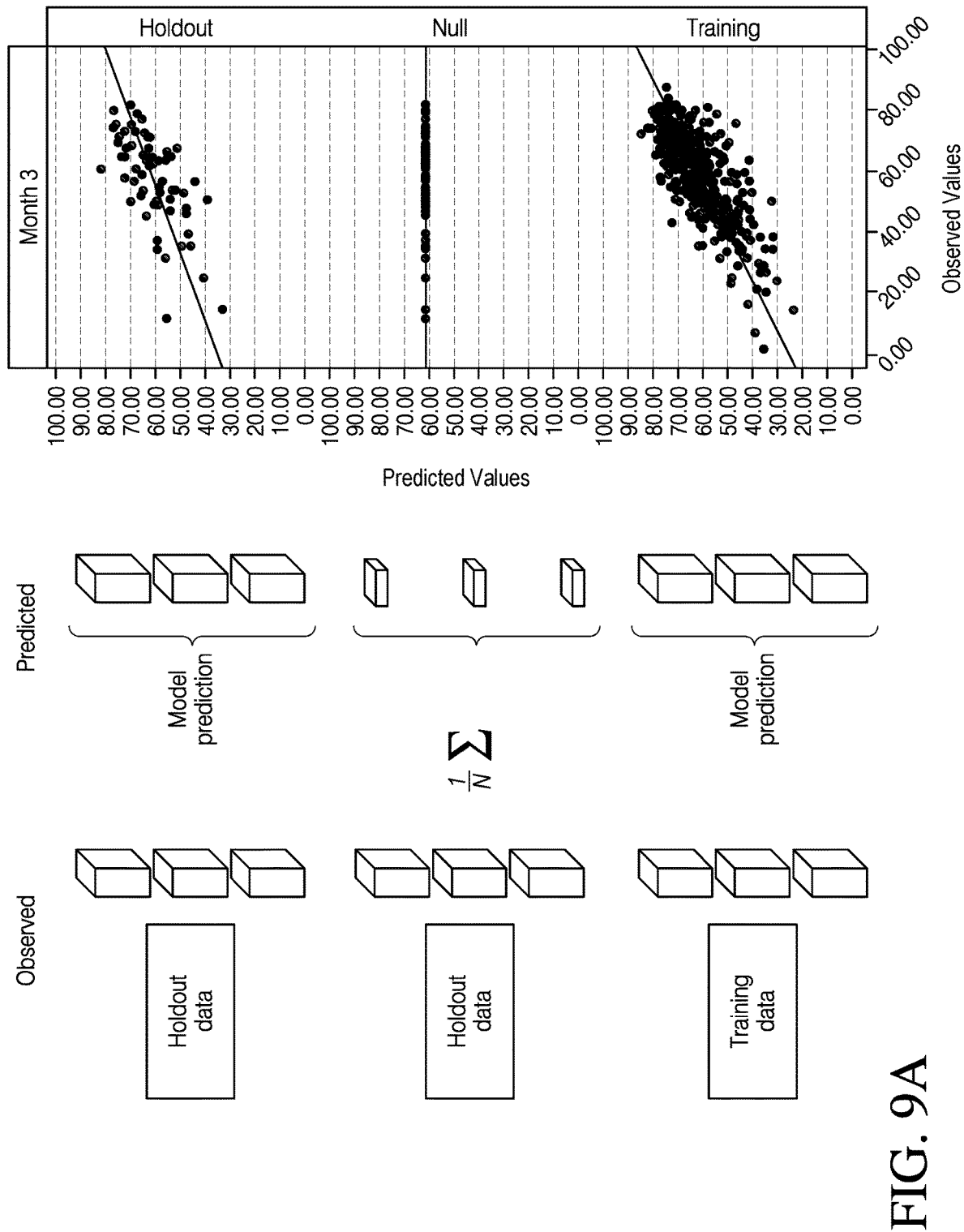
FIG. 9A shows BCVA values predicted by the RNN versus observed BCVA values for the holdout dataset at 3 months after administration of a dose of ranibizumab, in accordance with various embodiments.
Figure 9B:
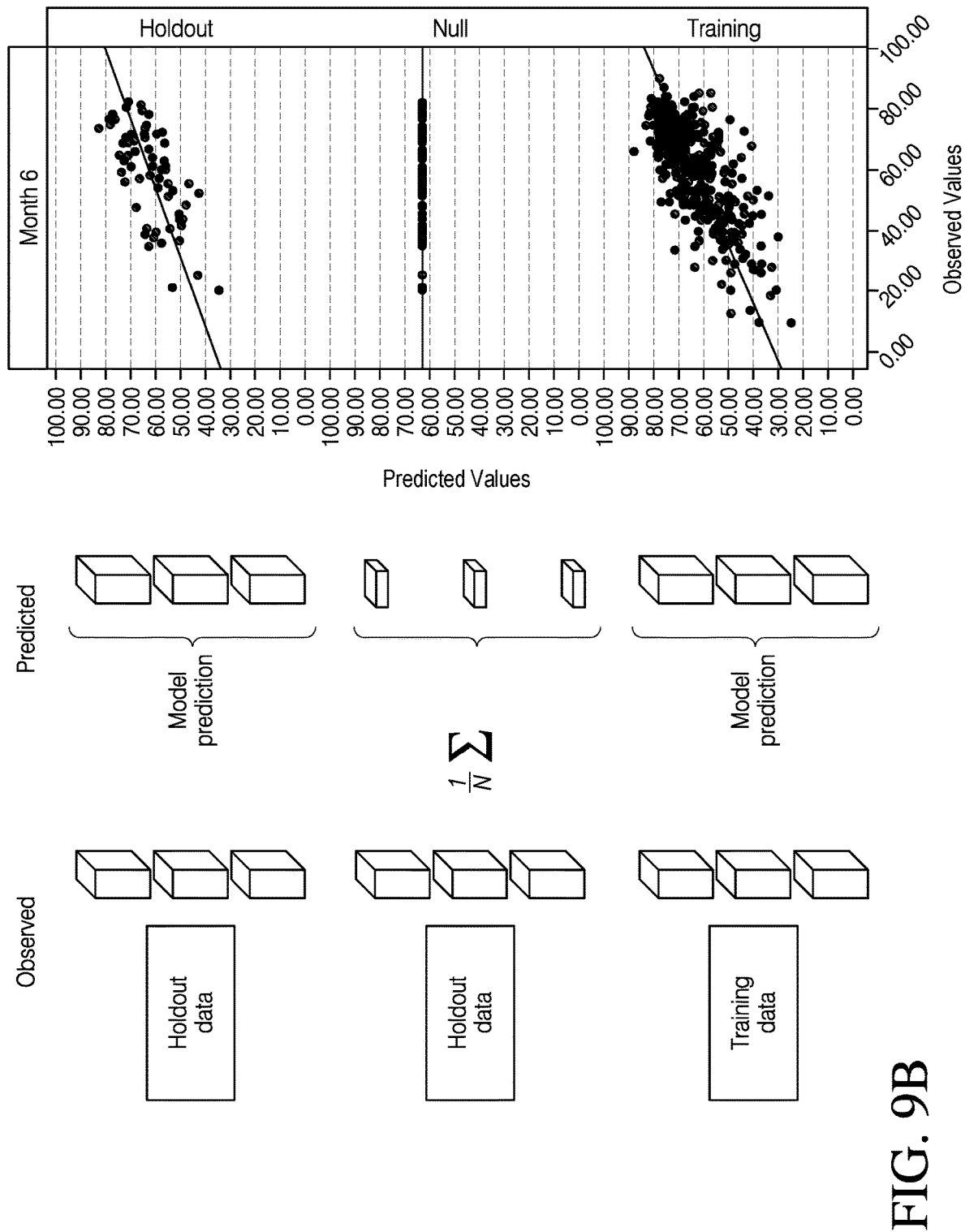
FIG. 9B shows BCVA values predicted by the RNN versus observed BCVA values for the holdout dataset at 6 months after administration of a dose of ranibizumab, in accordance with various embodiments.
Figure 9C:
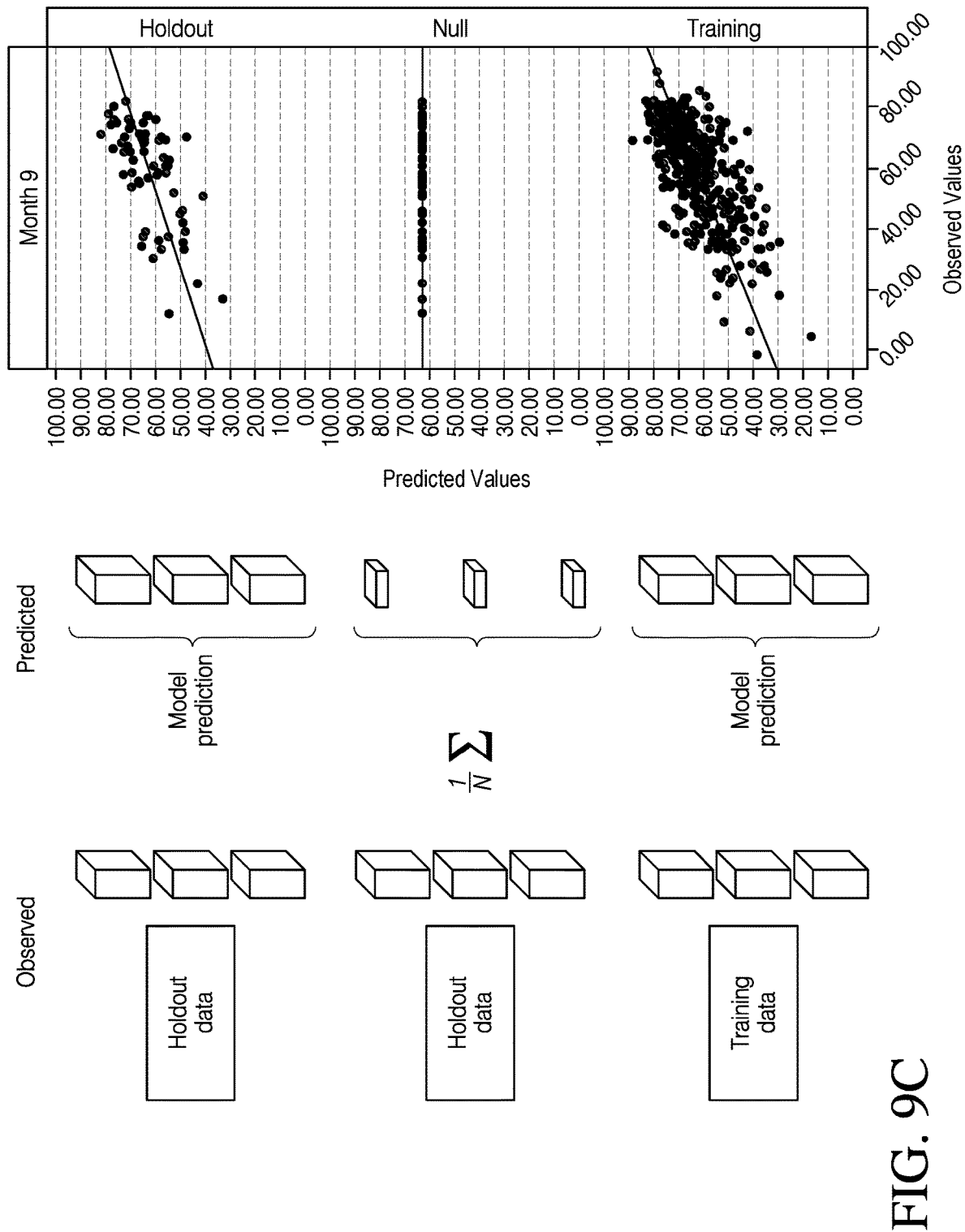
FIG. 9C shows BCVA values predicted by the RNN versus observed BCVA values for the holdout dataset at 9 months after administration of a dose of ranibizumab, in accordance with various embodiments.
Figure 9D:
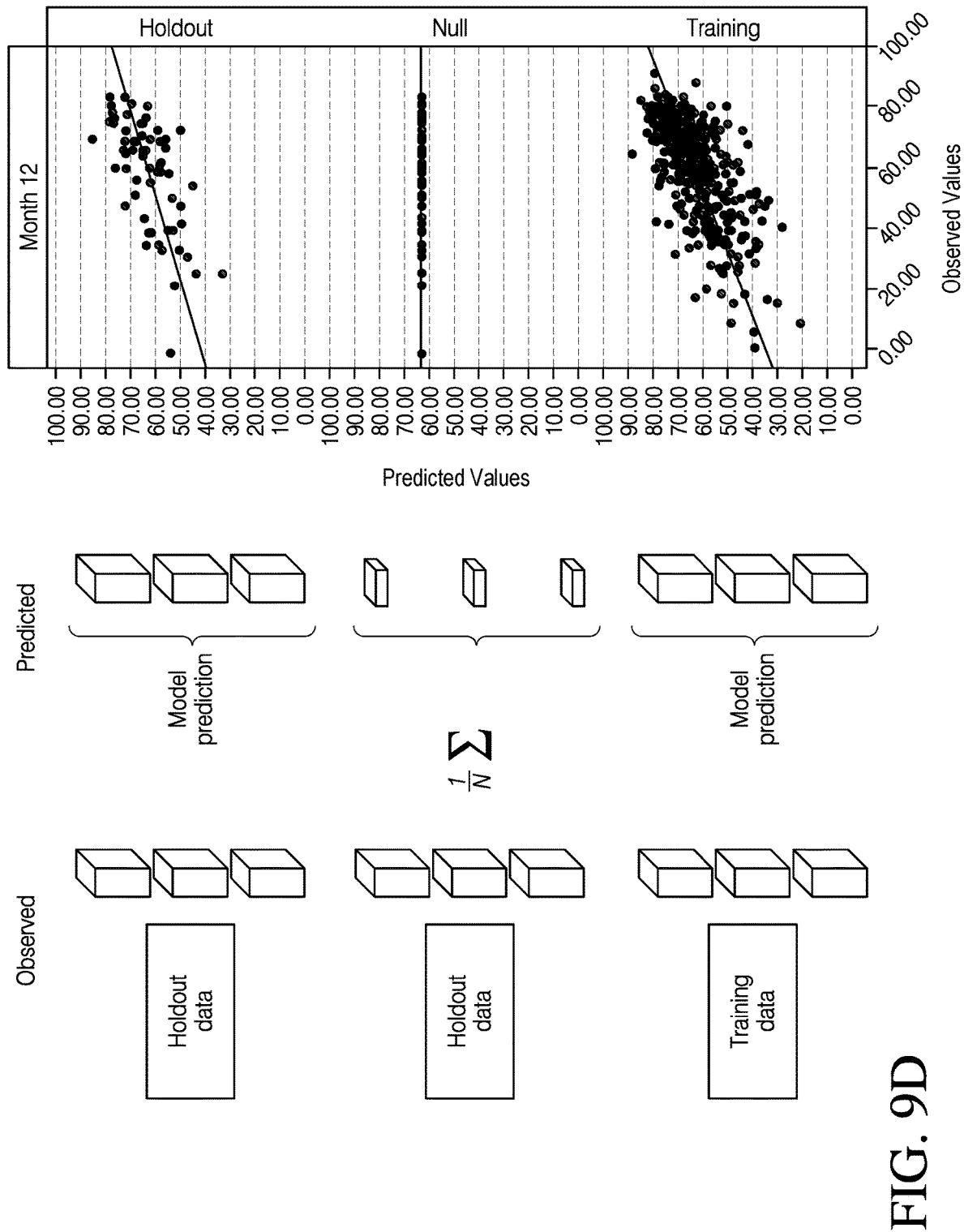
FIG. 9D shows BCVA values predicted by the RNN versus observed BCVA values for the holdout dataset at 12 months after administration of a dose of ranibizumab, in accordance with various embodiments.

FIG. 8 shows BCVA values predicted by the RNN versus observed BCVA values for holdout and training datasets. The predicted and observed BCVA values correspond to a point in time approximately 12 months after administration of the 0.5 mg or 2 mg dose of ranibizumab. As shown in FIGS. 7A-B, the predicted BCVA values corresponded well with both holdout ($r^2$=0.45, RMSE=13.98, MAE=10.81, Pearson correlation coefficient=0.67) and training ($r^2$=0.48, RMSE=12.29, MAE=9.39, Pearson correlation coefficient=0.69) datasets.

FIGS. 9A-D show BCVA values predicted by the RNN versus observed BCVA values for the holdout dataset at 3, 6, 9, and 12 months, respectively, after administration of a dose of ranibizumab. As shown in FIGS. 9A-D, the predicted BCVA values corresponded well with the holdout dataset.

Machine Learning

ML generally refers to any system or analytical and/or statistical procedure that may progressively improve computer performance of a task in an iterative manner. Examples of ML processes include supervised learning, reinforcement learning, unsupervised learning, and/or the like.

For example, an ML process may comprise a trained algorithm that is trained through supervised learning (e.g., various parameters are determined as weights or scaling factors after statistical determination of the weights or scaling factors using a training set comprising labeled examples). The ML process may comprise one or more of regression analysis, regularization, classification, dimensionality reduction, ensemble learning, meta learning, association rule learning, cluster analysis, anomaly detection, DL, or ultra-DL. The ML process may comprise, but is not limited to: k-means, k-means clustering, k-nearest neighbors, learning vector quantization, linear regression, non-linear regression, least squares regression, partial least squares regression, logistic regression, stepwise regression, multivariate adaptive regression splines, ridge regression, principle component regression, least absolute shrinkage and selection operation, least angle regression, canonical correlation analysis, factor analysis, independent component analysis, linear discriminant analysis, multidimensional scaling, non-negative matrix factorization, principal components analysis, principal coordinates analysis, projection pursuit, Sammon mapping, t-distributed stochastic neighbor embedding, AdaBoosting, boosting, gradient boosting, bootstrap aggregation, ensemble averaging, decision trees, conditional decision trees, boosted decision trees, gradient boosted decision trees, random forests, stacked generalization, Bayesian networks, Bayesian belief networks, naïve Bayes, Gaussian naïve Bayes, multinomial naïve Bayes, hidden Markov models, hierarchical hidden Markov models, support vector machines, encoders, decoders, auto-encoders, stacked auto-encoders, perceptrons, multi-layer perceptrons, artificial neural networks, feedforward neural networks, convolutional neural networks, recurrent neural networks, long short-term memory, deep belief networks, deep Boltzmann machines, deep convolutional neural networks, deep recurrent neural networks, or generative adversarial networks.

Computer-Implemented System

In various embodiments, at least a portion of the methods for predicting a subject response to a therapeutic can be implemented via software, hardware, firmware, or a combination thereof.

Figure 10:
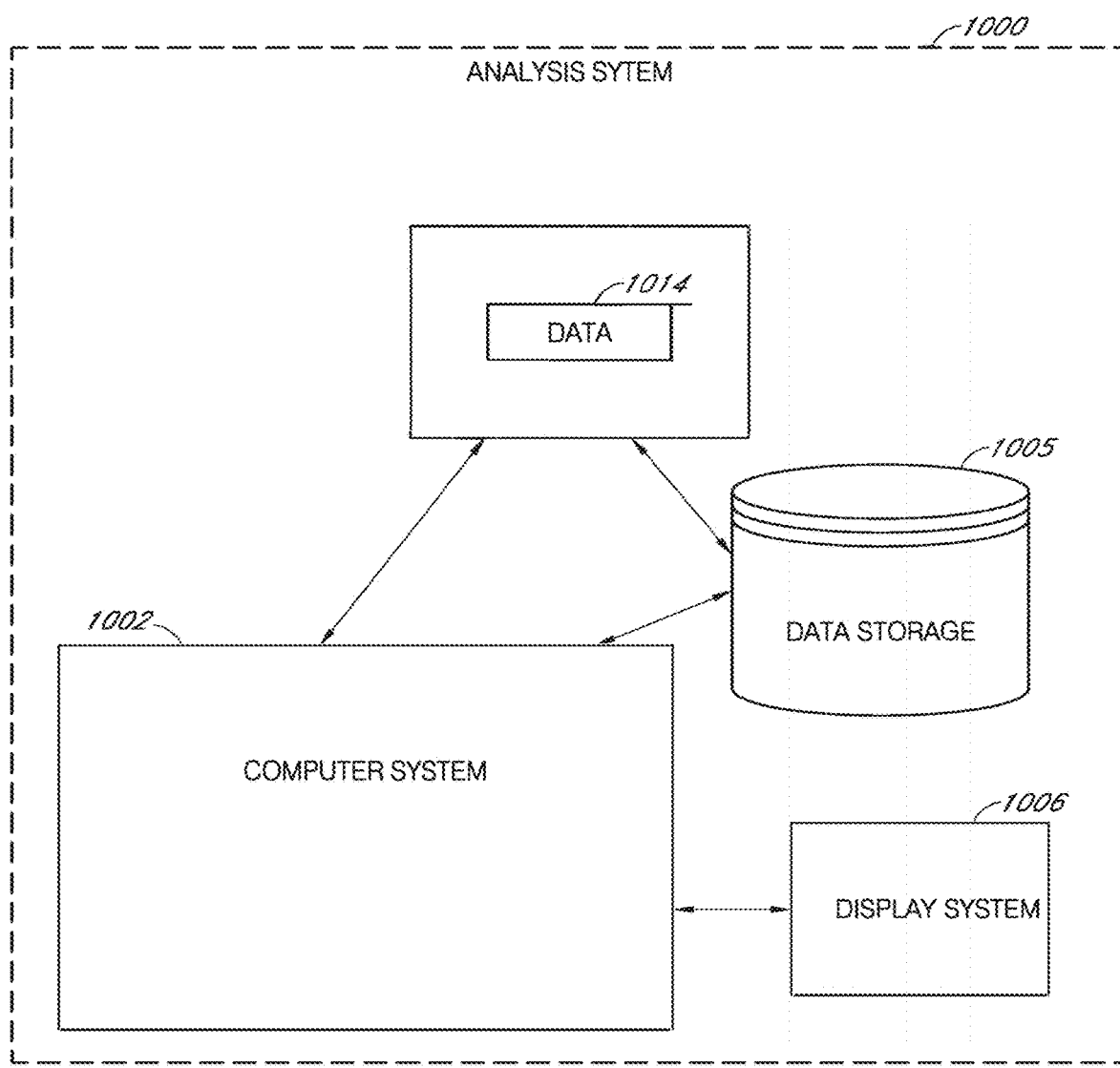
FIG. 10 is a block diagram of a system for predicting a subject response to a therapeutic, in accordance with various embodiments.

That is, as depicted in FIG. 10, the methods disclosed herein can be implemented on a system 1000 for predicting a subject response to a therapeutic. The system 1000 may comprise a computer system such as computer system 1002 (e.g., a computing device/analytics server). In various embodiments, the computer system 1002 can be communicatively connected to a data storage 1005 and a display system 1006 via a direct connection or through a network connection (e.g., LAN, WAN, Internet, etc.). The computer system 1002 can be configured to receive data, such as image feature data described herein. It should be appreciated that the computer system 1002 depicted in FIG. 10 can comprise additional engines or components as needed by the particular application or system architecture.

Figure 11:
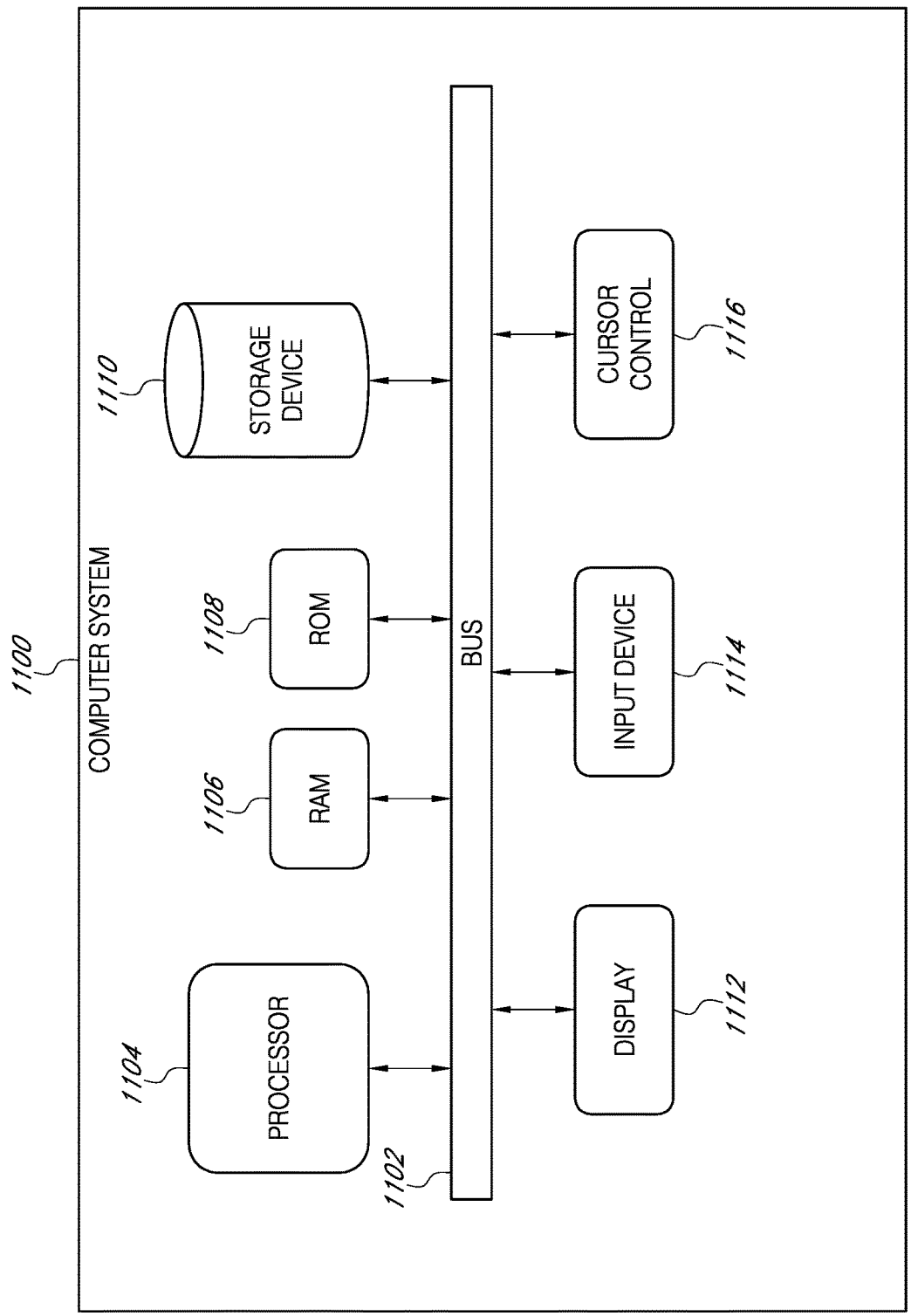
FIG. 11 is a block diagram of a computer system, in accordance with various embodiments.

FIG. 11 is a block diagram of a computer system in accordance with various embodiments. Computer system 1100 may be an example of one implementation for computer system 1002 described above in FIG. 10. In one or more examples, computer system 1100 can include a bus 1102 or other communication mechanism for communicating information, and a processor 1104 coupled with bus 1102 for processing information. In various embodiments, computer system 1100 can also include a memory, which can be a random access memory (RAM) 1106 or other dynamic storage device, coupled to bus 1102 for determining instructions to be executed by processor 1104. Memory also can be used for storing temporary variables or other intermediate information during execution of instructions to be executed by processor 1104. In various embodiments, computer system 1100 can further include a read only memory (ROM) 1108 or other static storage device coupled to bus 1102 for storing static information and instructions for processor 1104. A storage device 1110, such as a magnetic disk or optical disk, can be provided and coupled to bus 1102 for storing information and instructions.

In various embodiments, computer system 1100 can be coupled via bus 1102 to a display 1112, such as a cathode ray tube (CRT) or liquid crystal display (LCD), for displaying information to a computer user. An input device 1114, including alphanumeric and other keys, can be coupled to bus 1102 for communicating information and command selections to processor 1104. Another type of user input device is a cursor control 1116, such as a mouse, a joystick, a trackball, a gesture input device, a gaze-based input device, or cursor direction keys for communicating direction information and command selections to processor 1104 and for controlling cursor movement on display 1112.

Consistent with certain implementations of the present teachings, results can be provided by computer system 1100 in response to processor 1104 executing one or more sequences of one or more instructions contained in RAM 1106. Such instructions can be read into RAM 1106 from another computer-readable medium or computer-readable storage medium, such as storage device 1110. Execution of the sequences of instructions contained in RAM 1106 can cause processor 1104 to perform the processes described herein. Alternatively, hard-wired circuitry can be used in place of or in combination with software instructions to implement the present teachings. Thus, implementations of the present teachings are not limited to any specific combination of hardware circuitry and software.

The term "computer-readable medium" (e.g., data store, data storage, storage device, data storage device, etc.) or "computer-readable storage medium" as used herein refers to any media that participates in providing instructions to processor 1104 for execution. Such a medium can take many forms, including but not limited to, non-volatile media, volatile media, and transmission media. Examples of non-volatile media can include, but are not limited to, optical, solid state, magnetic disks, such as storage device 1110. Examples of volatile media can include, but are not limited to, dynamic memory, such as RAM 1106. Examples of transmission media can include, but are not limited to, coaxial cables, copper wire, and fiber optics, including the wires that comprise bus 1102.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 1104 of computer system 1100 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, optical communications connections, etc.

It should be appreciated that the methodologies described herein, flow charts, diagrams, and accompanying disclosure can be implemented using computer system 1100 as a standalone device or on a distributed network of shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 1100, whereby processor 1104 would execute the analyses and determinations provided by these engines, subject to instructions provided by any one of, or a combination of, the memory components RAM 1106, ROM 1108, or storage device 1110 and user input provided via input device 1114.

RECITATION OF EMBODIMENTS

Embodiment 1. A method for predicting a subject response to a therapeutic, comprising:
  receiving, by one or more processors, image feature data from at least one time point associated with an administration of the therapeutic to at least one test subject; and
  generating, by the one or more processors, a plurality of predicted time-series responses of the at least one test subject to the administered therapeutic using a ML component trained using a training data set comprising a plurality of time-series responses of at least one training subject and corresponding image features of the at least one training subject after an administration of a therapeutic, each corresponding image feature associated with a time-series response of the plurality of time-series responses.

Embodiment 2. The method of Embodiment 1, wherein the ML component comprises a neural network (NN).

Embodiment 3. The method of Embodiment 2, wherein the NN comprises a recurrent NN (RNN).

Embodiment 4. The method of any one of Embodiments 1-3, wherein the training data set further comprises at least an age of the at least one training subject.

Embodiment 5. The method of any one of Embodiments 1-4, wherein the plurality of time-series responses comprises a plurality of best corrected visual acuity (BCVA) scores of the at least one training subject or wherein the plurality of predicted time-series responses comprises a plurality of best corrected visual acuity (BCVA) scores of the at least one test subject.

Embodiment 6. The method of any one of Embodiments 1-5, wherein the image features or the image feature data comprises at least one parameter obtained from at least one optical coherence tomography (OCT) image.

Embodiment 7. The method of Embodiment 6, wherein the at least one OCT image comprises at least one spectral domain-OCT (SD-OCT) image.

Embodiment 8. The method of Embodiment 6 or 7, wherein the parameter comprises an intraretinal fluid (IRF) value, a subretinal fluid (SRF) value, a subretinal hyperreflective material (SHRM) material, or a pigment epithelial detachment (PED) value.

Embodiment 9. The method of any one of Embodiments 1-8, wherein the therapeutic comprises administration of a drug.

Embodiment 10. The method of Embodiment 9, wherein the drug corresponds to an ophthalmic disorder.

Embodiment 11. The method of Embodiment 10, wherein the ophthalmic disorder comprises a macular degeneration disorder.

Embodiment 12. The method of any one of Embodiments 1-11, further comprising generating the training data set by measuring the plurality of time-series responses of the at least one training subject and the corresponding image features.

Embodiment 13. A system for predicting a subject response to a therapeutic, comprising:
  a non-transitory memory; and
  one or more processors coupled to the non-transitory memory and configured to read instructions from the non-transitory memory to cause the system to perform operations comprising:
    receiving image feature data from at least one time point associated with an administration of the therapeutic to at least one test subject; and
    generating a plurality of predicted time-series responses of the at least one test subject to the administered therapeutic using a ML component trained using a training data set comprising a plurality of time-series responses of at least one training subject and corresponding image features of the at least one training subject after an administration of a therapeutic, each corresponding image feature associated with a time-series response of the plurality of time-series responses.

Embodiment 14. The system of Embodiment 13, wherein the ML component comprises a neural network (NN).

Embodiment 15. The system of Embodiment 14, wherein the NN comprises a recurrent NN (RNN).

Embodiment 16. The system of any one of Embodiments 13-15, wherein the training data set further comprises at least an age of the at least one training subject.

Embodiment 17. The system of any one of Embodiments 13-16, wherein the plurality of time-series responses comprises a plurality of best corrected visual acuity (BCVA) scores of the at least one training subject or wherein the plurality of predicted time-series responses comprises a plurality of best corrected visual acuity (BCVA) scores of the at least one test subject.

Embodiment 18. The system of any one of Embodiments 13-17, wherein the image features or the image feature data comprises at least one parameter obtained from at least one optical coherence tomography (OCT) image.

Embodiment 19. The system of Embodiment 18, wherein the at least one OCT image comprises at least one spectral domain-OCT (SD-OCT) image.

Embodiment 20. The system of Embodiment 18 or 19, wherein the parameter comprises an intraretinal fluid (IRF) value, a subretinal fluid (SRF) value, a subretinal hyperreflective material (SHRM) material, or a pigment epithelial detachment (PED) value.

Embodiment 21. The system of any one of Embodiments 13-20, wherein the therapeutic comprises administration of a drug.

Embodiment 22. The system of Embodiment 21, wherein the drug corresponds to an ophthalmic disorder.

Embodiment 23. The system of Embodiment 22, wherein the ophthalmic disorder comprises a macular degeneration disorder.

Embodiment 24. The system of any one of Embodiments 13-23, wherein the operations further comprise generating the training data set by measuring the plurality of time-series responses of the at least one training subject and the corresponding image features.

Embodiment 25. A non-transitory, machine-readable medium having stored thereon machine-readable instructions executable to cause a system to perform operations comprising:
  receiving image feature data from at least one time point associated with an administration of the therapeutic to at least one test subject; and
  generating a plurality of predicted time-series responses of the at least one test subject to the administered therapeutic using a ML component trained using a training data set comprising a plurality of time-series responses of at least one training subject and corresponding image features of the at least one training subject after an administration of a therapeutic, each corresponding image feature associated with a time-series response of the plurality of time-series responses.

Embodiment 26. The non-transitory, machine-readable medium of Embodiment 25, wherein the ML component comprises a neural network (NN).

Embodiment 27. The non-transitory, machine-readable medium of Embodiment 26, wherein the NN comprises a recurrent NN (RNN).

Embodiment 28. The non-transitory, machine-readable medium of any one of Embodiments 25-27, wherein the training data set further comprises at least an age of the at least one training subject.

Embodiment 29. The non-transitory, machine-readable medium of any one of Embodiment 25-28, wherein the plurality of time-series responses comprises a plurality of best corrected visual acuity (BCVA) scores of the at least one training subject or wherein the plurality of predicted time-series responses comprises a plurality of best corrected visual acuity (BCVA) scores of the at least one test subject.

Embodiment 30. The non-transitory, machine-readable medium of any one of Embodiment 25-29, wherein the image features or the image feature data comprises at least one parameter obtained from at least one optical coherence tomography (OCT) image.

Embodiment 31. The non-transitory, machine-readable medium of Embodiment 30, wherein the at least one OCT image comprises at least one spectral domain-OCT (SD-OCT) image.

Embodiment 32. The non-transitory, machine-readable medium of Embodiment 30 or 31, wherein the parameter comprises an intraretinal fluid (IRF) value, a subretinal fluid (SRF) value, a subretinal hyperreflective material (SHRM) material, or a pigment epithelial detachment (PED) value.

Embodiment 33. The non-transitory, machine-readable medium of any one of Embodiments 25-32, wherein the therapeutic comprises administration of a drug.

Embodiment 34. The non-transitory, machine-readable medium of Embodiment 33, wherein the drug corresponds to an ophthalmic disorder.

Embodiment 35. The non-transitory, machine-readable medium of Embodiment 34, wherein the ophthalmic disorder comprises a macular degeneration disorder.

Embodiment 36. The non-transitory, machine-readable medium of any one of Embodiments 25-35, wherein the operations further comprise generating the training data set by measuring the plurality of time-series responses of the at least one training subject and the corresponding image features.

What is claimed is:

1. A method comprising:
receiving, by one or more processors, image feature data from a baseline time point at which ranibizumab is administered to a plurality of subjects for treating an ophthalmic disorder;
generating, by the one or more processors, a plurality of predicted time-series responses of the plurality of subjects to the ranibizumab using the image feature data and a machine learning (ML) model trained using a training data set comprising a plurality of time-series responses of a plurality of training subjects and corresponding image features of the plurality of training subjects after an administration of the ranibizumab, each corresponding image feature associated with a time-series response of the plurality of time-series responses,
wherein each predicted time-series response of the plurality of predicted time-series responses includes a plurality of predicted best corrected visual acuity (BCVA) values for a plurality of time points after the baseline time point;
identifying a first group of subjects from the plurality of subjects that have predicted BCVA values of the plurality of predicted BCVA values that are above an initial BCVA value corresponding to the baseline time point for exclusion from a clinical trial;
wherein a portion of the plurality of subjects remaining after the first group of subjects is excluded is used to form a second group of subjects; and
administering a therapeutic that is different from the ranibizumab to the second group of subjects in the clinical trial.

2. The method of claim 1, wherein the ML model comprises a neural network (NN).

3. The method of claim 2, wherein the NN comprises a recurrent NN (RNN).

4. The method of claim 1, wherein the training data set further comprises ages of the plurality of training subjects.

5. The method of claim 1, wherein the image feature data comprises at least one parameter obtained from at least one optical coherence tomography (OCT) image.

6. The method of claim 5, wherein the at least one OCT image comprises at least one spectral domain-OCT (SD-OCT) image.

7. The method of claim 5, wherein the parameter comprises an intraretinal fluid (IRF) value, a subretinal fluid (SRF) value, a subretinal hyperreflective material (SHRM) material value, or a pigment epithelial detachment (PED) value.

8. The method of claim 1, wherein the therapeutic that is different from the ranibizumab comprises a drug treatment for macular degeneration.

9. The method of claim 1, wherein the ophthalmic disorder comprises macular degeneration.

10. The method of claim 9, wherein the macular degeneration comprises a subfoveal neovascular age-related macular degeneration disorder.

11. The method of claim 1, further comprising:
generating the training data set by measuring the plurality of time-series responses of the plurality of training subjects and the corresponding image features.

12. A system comprising:
a non-transitory memory; and
one or more processors coupled to the non-transitory memory and configured to read instructions from the non-transitory memory to cause the system to perform operations comprising:
receiving image feature data from a baseline time point at which ranibizumab is administered to a plurality of subjects for treating an ophthalmic disorder;
generating a plurality of predicted time-series responses of the plurality of subjects to the ranibizumab using the image feature data and a machine learning (ML) model trained using a training data set comprising a plurality of time-series responses of a plurality of training subjects and corresponding image features of the plurality of training subjects after an administration of the ranibizumab, each corresponding image feature associated with a time-series response of the plurality of time-series responses,
wherein each predicted time-series response of the plurality of predicted time-series responses includes a plurality of predicted best corrected visual acuity (BCVA) values for a plurality of time points after the baseline time point;
identifying a first group of subjects from the plurality of subjects that have predicted BCVA values of the plurality of predicted BCVA values that are above an initial BCVA value corresponding to the baseline time point for exclusion from a clinical trial;
identifying a portion of the plurality of subjects remaining after the first group of subjects is excluded as a second group of subjects,
wherein a therapeutic that is different from the ranibizumab is to be administered to the second group of subjects in the clinical trial.

13. The system of claim 12, wherein the ML model comprises a neural network (NN).

14. The system of claim 13, wherein the NN comprises a recurrent NN (RNN).

15. The system of claim 12, wherein the training data set further comprises ages of the plurality of training subjects.

16. A non-transitory, machine-readable medium having stored thereon machine-readable instructions executable to cause a system to perform operations comprising:

receiving image feature data from a baseline time point at which ranibizumab is administered a plurality of subjects for treating an ophthalmic disorder;

generating a plurality of predicted time-series responses of the plurality of subjects to the ranibizumab using the image feature data and a machine learning (ML) model trained using a training data set comprising a plurality of time-series responses of a plurality of training subjects and corresponding image features of the plurality of training subjects after an administration of the ranibizumab, each corresponding image feature associated with a time-series response of the plurality of time-series responses, wherein each predicted time-series response of the plurality of predicted time-series responses includes a plurality of predicted best corrected visual acuity (BCVA) values for a plurality of time points after the baseline time point;

identifying a first group of subjects from the plurality of subjects that have predicted BCVA values of the plurality of predicted BCVA values that are above an initial BCVA value corresponding to the baseline time point for exclusion from a clinical trial;

identifying a portion of the plurality of subjects remaining after the first group of subjects is excluded as a second group of subjects, wherein a therapeutic that is different from the ranibizumab is to be administered to the second group of subjects in the clinical trial.

17. The non-transitory, machine-readable medium of claim 16, wherein the ML model comprises a neural network (NN).

18. The non-transitory, machine-readable medium of claim 17, wherein the NN comprises a recurrent NN (RNN).

19. The system of claim 12, wherein the image feature data comprises at least one parameter obtained from at least one optical coherence tomography (OCT) image.

20. The system of claim 19, wherein the at least one OCT image comprises at least one spectral domain-OCT (SD-OCT) image and wherein the parameter comprises an intraretinal fluid (IRF) value, a subretinal fluid (SRF) value, a subretinal hyperreflective material (SHRM) material value, or a pigment epithelial detachment (PED) value.

* * * * *